United States Patent
Rundquist et al.

(10) Patent No.: US 9,265,920 B2
(45) Date of Patent: Feb. 23, 2016

(54) BALLOON CATHETER WITH IMPROVED PUSHABILITY

(75) Inventors: Charles Rundquist, White Bear Lake, MN (US); Eric Petersen, Maple Grove, MN (US); Jeffry Johnson, Plymouth, MN (US); Roger W. McGowan, Otsego, MN (US); Chuanjing Xu, Chaska, MN (US); Adam D. Grovender, Brooklyn Park, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 242 days.

(21) Appl. No.: 13/475,763

(22) Filed: May 18, 2012

(65) Prior Publication Data

US 2012/0296366 A1 Nov. 22, 2012

Related U.S. Application Data

(60) Provisional application No. 61/488,533, filed on May 20, 2011.

(51) Int. Cl.
| | |
|---|---|
| *A61M 29/02* | (2006.01) |
| *A61M 25/10* | (2013.01) |
| *A61M 25/00* | (2006.01) |
| *A61M 25/01* | (2006.01) |

(52) U.S. Cl.
CPC ......... *A61M 25/1036* (2013.01); *A61M 25/005* (2013.01); *A61M 25/0029* (2013.01); *A61M 25/0032* (2013.01); *A61M 2025/0034* (2013.01); *A61M 2025/0037* (2013.01); *A61M 2025/0059* (2013.01); *A61M 2025/0183* (2013.01); *Y10T 29/49826* (2015.01)

(58) Field of Classification Search
CPC ............ A61M 2025/0034; A61M 2025/0037; A61M 2025/0059; A61M 2025/0183; A61M 25/0029; A61M 25/0032; A61M 25/005
USPC ................ 606/192, 191; 604/96.01; 623/1.11
See application file for complete search history.

(56) References Cited

U.S. PATENT DOCUMENTS

| | | | |
|---|---|---|---|
| 5,156,594 | A | 10/1992 | Keith |
| 5,238,004 | A | 8/1993 | Sahatjian et al. |
| 5,328,472 | A * | 7/1994 | Steinke et al. ........... 604/102.02 |
| 5,720,724 | A | 2/1998 | Ressemann et al. |
| 5,772,609 | A | 6/1998 | Nguyen et al. |
| 6,139,510 | A | 10/2000 | Palermo |

(Continued)

FOREIGN PATENT DOCUMENTS

| | | |
|---|---|---|
| EP | 1479409 A1 | 11/2004 |
| EP | 1787673 A1 | 5/2007 |
| WO | 9402194 A1 | 2/1994 |

*Primary Examiner* — Thomas McEvoy
*Assistant Examiner* — Julie A Szpira
(74) *Attorney, Agent, or Firm* — Seager, Tufte & Wickhem, LLP (57) ABSTRACT

Balloon catheter and methods for making and using balloon catheters are disclosed. An example balloon catheter may include a proximal shaft. A midshaft may be attached to the proximal shaft. The midshaft may have an outer wall. A distal shaft may be attached to the midshaft. A balloon may be coupled to the distal shaft. An inflation lumen may be defined that extends from the proximal shaft, through the midshaft, and into the distal shaft. The inflation lumen may be in fluid communication with the balloon. A core wire may be disposed within the inflation lumen and may be attached to the midshaft.

13 Claims, 11 Drawing Sheets

(56) References Cited

U.S. PATENT DOCUMENTS

| | | |
|---|---|---|
| 6,361,529 B1 | 3/2002 | Goodin et al. |
| 6,409,863 B1 | 6/2002 | Williams et al. |
| 6,475,187 B1 | 11/2002 | Gerberding |
| 6,508,803 B1 | 1/2003 | Horikawa et al. |
| 7,901,378 B2 | 3/2011 | Solar et al. |
| 8,057,430 B2 | 11/2011 | Grovender et al. |
| 2004/0267196 A1* | 12/2004 | Miki et al. ............... 604/103.04 |
| 2007/0027524 A1* | 2/2007 | Johnson et al. .............. 623/1.11 |
| 2007/0083132 A1* | 4/2007 | Sharrow ....................... 600/585 |
| 2008/0082050 A1* | 4/2008 | Solar et al. ............... 604/164.13 |
| 2009/0270802 A1* | 10/2009 | Nishide et al. ........... 604/103.05 |
| 2010/0217234 A1* | 8/2010 | Grovender et al. ........... 604/523 |

* cited by examiner

BALLOON CATHETER WITH IMPROVED PUSHABILITY

CROSS-REFERENCE TO RELATED APPLICATION

This application claims priority under 35 U.S.C. §119 to U.S. Provisional Application Ser. No. 61/488,533, filed May 20, 2011, the entirety of which is incorporated herein by reference.

TECHNICAL FIELD

The present invention relates generally to catheters for performing medical procedures. More particularly, the present invention relates to balloon catheters.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices. An example medical device may include a balloon catheter. An example balloon catheter may include a proximal shaft. A midshaft may be attached to the proximal shaft. The midshaft may have an outer wall. A distal shaft may be attached to the midshaft. A balloon may be coupled to the distal shaft. An inflation lumen may be defined that extends from the proximal shaft, through the midshaft, and into the distal shaft. The inflation lumen may be in fluid communication with the balloon. A core wire may be disposed within the inflation lumen and may be attached to the midshaft.

Another example balloon catheter may include a catheter shaft having a distal region and an inner wall surface defining an inflation lumen. A balloon may be attached to the distal region. The balloon may be in fluid communication with the inflation lumen. A core wire may be disposed within the inflation lumen. The core wire may be attached to the inner wall surface at a plurality of discrete bond points.

An example method for manufacturing a catheter may include providing a catheter shaft having a distal region and an inner wall surface defining an inflation lumen and attaching a balloon to the distal region. The balloon may be in fluid communication with the inflation lumen. The method may also include disposing a core wire within the inflation lumen and attaching the core wire to the inner wall surface of the catheter shaft.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Figure 1:
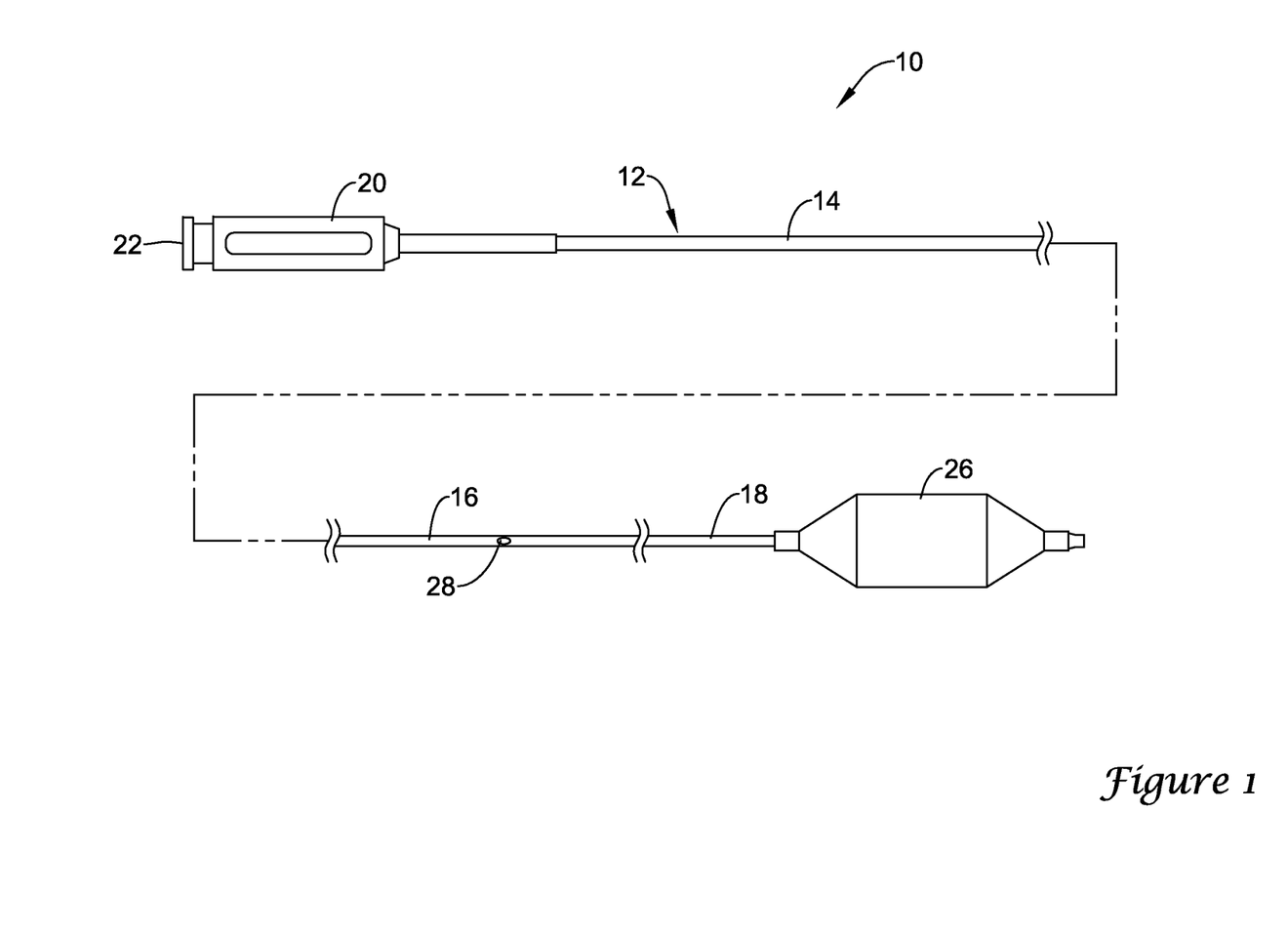
FIG. 1 is a plan view of an example balloon catheter.

FIG. 1 is a plan view of an example catheter 10, for example a balloon catheter. Catheter 10 may include a catheter shaft 12 having a proximal shaft portion 14, a midshaft portion 16 and a distal shaft portion 18. In some embodiments, proximal shaft portion 14 may be a metallic hypotube. Midshaft portion 16 may be fitted over, fitted within, or abut proximal shaft portion 14, as appropriate. Likewise, distal shaft portion 18 may be fitted over, fitted within, or abut midshaft portion 16. These are just examples as any suitable arrangement may be utilized. A hub 20 may be attached to proximal shaft portion 14. Hub 20 may include one or more ports such as, for example, a port 22.

Figure 2:
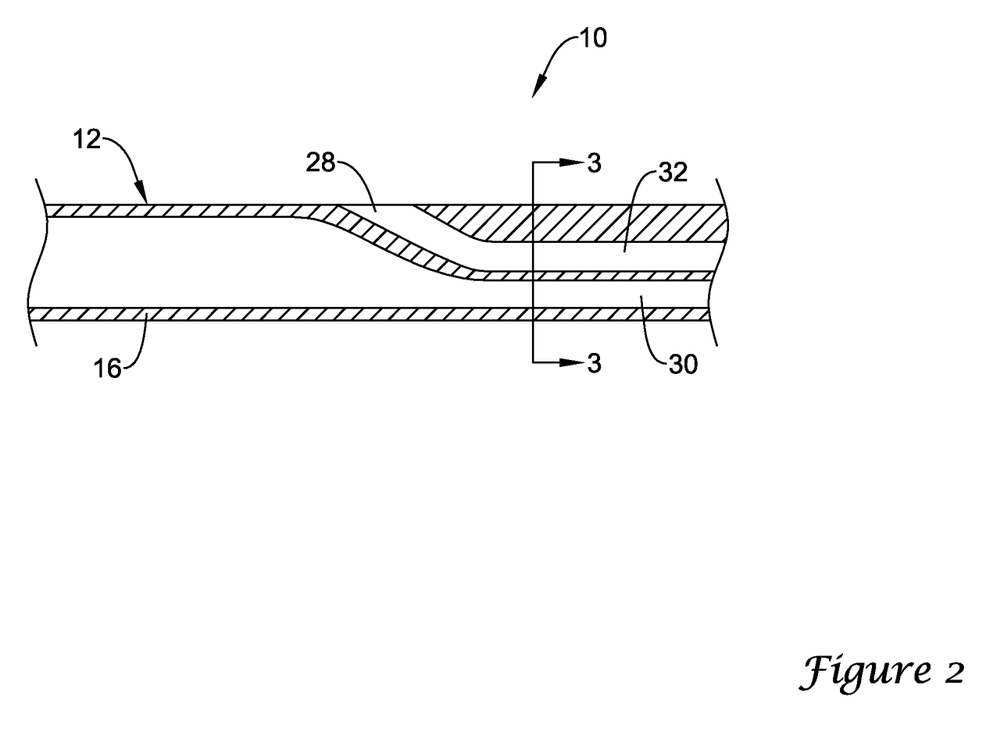
FIG. 2 is a cross-sectional view of a portion of the example balloon catheter shown in FIG. 1.
Figure 3:
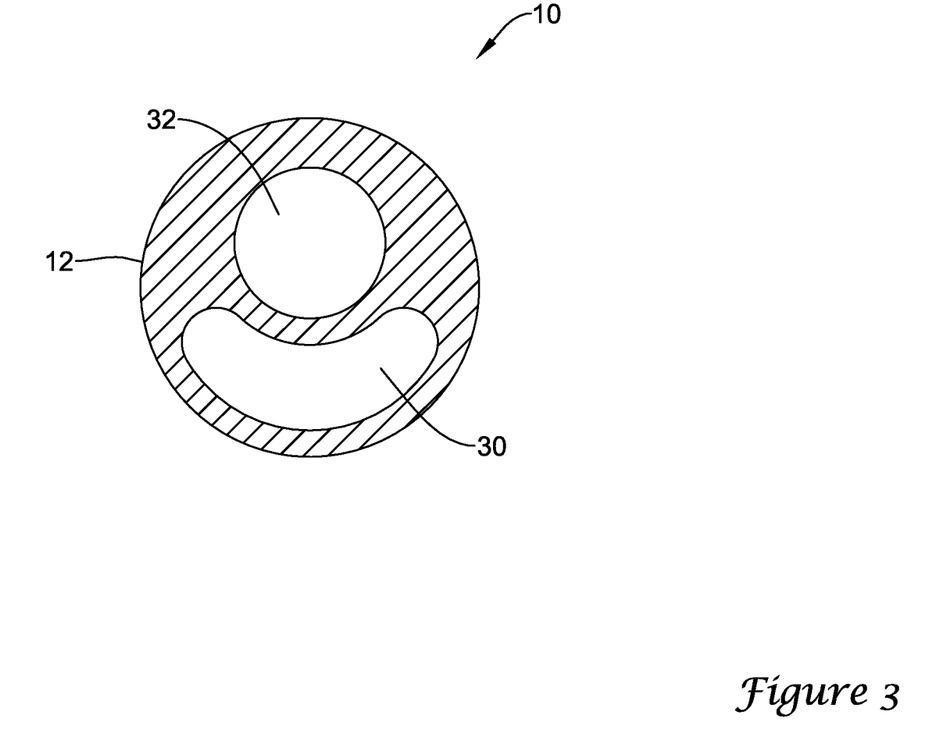
FIG. 3 is a cross-sectional view taken through line 3-3 in FIG. 2.

An expandable balloon 26 may be attached to distal shaft portion 18. Balloon 26 may be expanded by infusing inflation media through an inflation lumen 30, which is shown in FIG. 2. In at least some embodiments, port 22 may provide access to inflation lumen 30. Accordingly, a suitable inflation device may be attached to port 22 and inflation media may be passed through inflation lumen 30 to inflate balloon 26. Along a region of midshaft portion 16, inflation lumen 30 may have an annular shape as seen in FIG. 3. This may be due to the formation of a guidewire port 28 in midshaft portion 16. Some additional details regarding the formation of guidewire port 28 and/or inflation lumen 30 are provided herein.

As indicated above, guidewire port 28 may be formed in midshaft portion 16. For example, guidewire port 28 may be an opening extending through the wall of midshaft portion 16 that provides access to a guidewire lumen 32. In the embodiment depicted in FIG. 2, guidewire port 28 is positioned at a location that is distal to the proximal end of catheter shaft 12. When so arranged, catheter 10 may be a single-operator-exchange or rapid-exchange catheter, which allows catheter 10 to be used with a shorter guidewire. As such, guidewire lumen 32 may extend over only a portion of the length of catheter shaft 12. For example, guidewire lumen 32 may extend along distal shaft portion 18 and part of midshaft portion 16. Other embodiments, however, are contemplated where catheter 10 is an over-the-wire catheter or fixed wire catheter. In these embodiments, guidewire lumen 32 may extend along essentially the entire length of catheter shaft 12.

Catheters like catheter 10 may be designed to have increased or increasing distal flexibility. This may be desirable because portions of the catheter 10, particularly distal portions, may need to navigate sharp bends or turns within the vasculature. When the catheter shaft includes multiple sections or portions, however, the transition points between the sections may have a tendency to be more susceptible to kinking or buckling. For example, the transition point or points where the catheter shaft (e.g., catheter shaft 12) transitions from a relatively stiff proximal shaft portion (e.g., proximal shaft portion 14, which may take the form of a hypotube) to a more flexible midshaft and/or distal portion (e.g., midshaft portion 16 and/or distal shaft portion 18) may be susceptible to kinking and/or buckling.

In addition, because more distal portions of the catheter 10 may be designed to be highly flexible, it may be challenging to push the catheter through the vasculature in a reliable manner. In other words, increased distal flexibility, while being desirable for allowing the catheter to navigate the tortuous anatomy, may make it more difficult to "push" the catheter through the anatomy.

Figure 4:
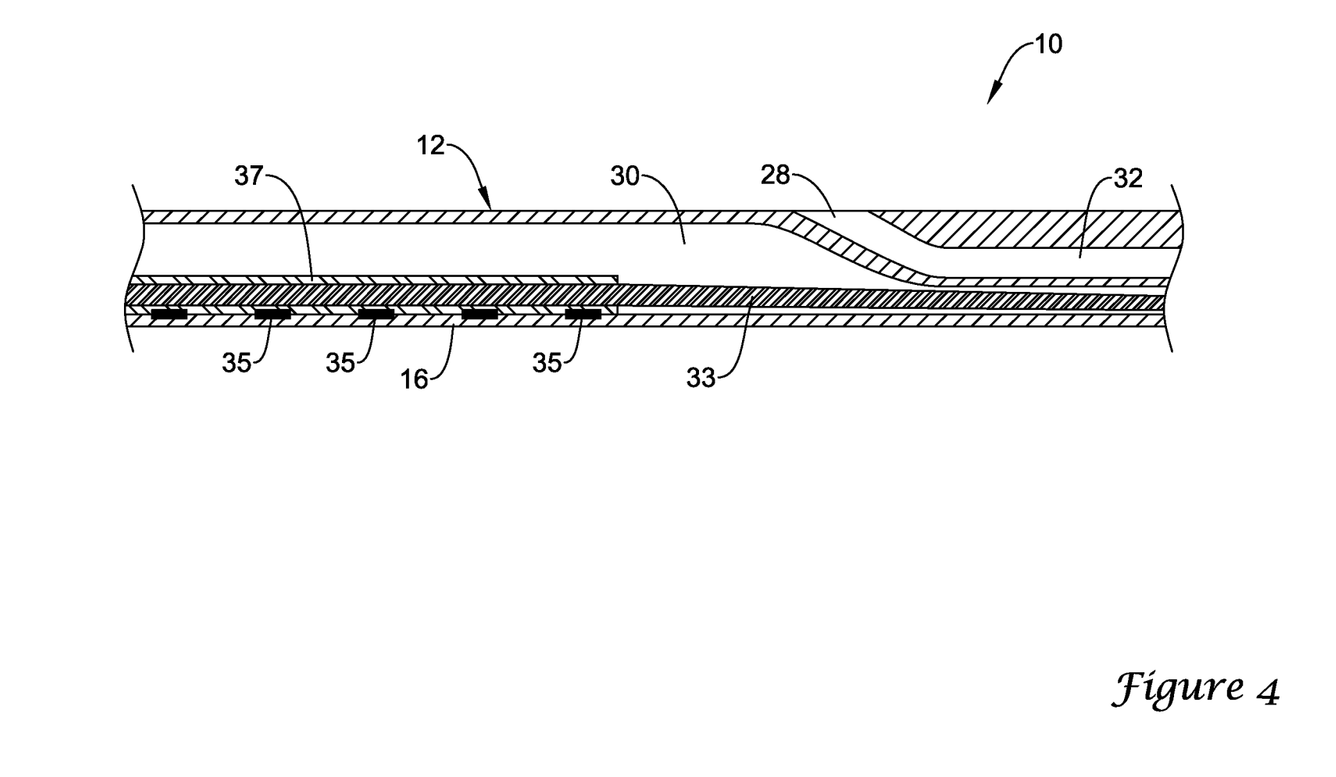
FIG. 4 is an alternative cross-sectional side view of a portion of the example balloon catheter shown in FIGS. 1-4.

In order to improve the transition in flexibility from proximal shaft portion 14 to midshaft portion 16 and/or distal shaft portion 18 and in order to make catheter shaft 12 more "pushable" through the anatomy, catheter shaft 12 may include a core wire 33 (not shown in FIG. 2, but illustrated in FIG. 4). Core wire 33 may take the form of a wire or rod that extends within inflation lumen 30 along an interior portion (e.g., along an inner wall surface) of catheter shaft 12. In at least some embodiments, core wire 33 extends from proximal shaft portion 14 to a position distally of guidewire port 28.

In order to further improve the flexibility transition and to further improve the pushability of catheter 10, core wire 33 is attached to the inner surface of catheter shaft 12. For example, core wire 33 may be attached to the inner surface of midshaft portion 16. Attachment between core wire 33 and catheter shaft 12 may occur in a variety of different manners including, for example, an adhesive bond, a thermal bond, a laser bond, a weld, combinations thereof, or the like.

Figure 5:
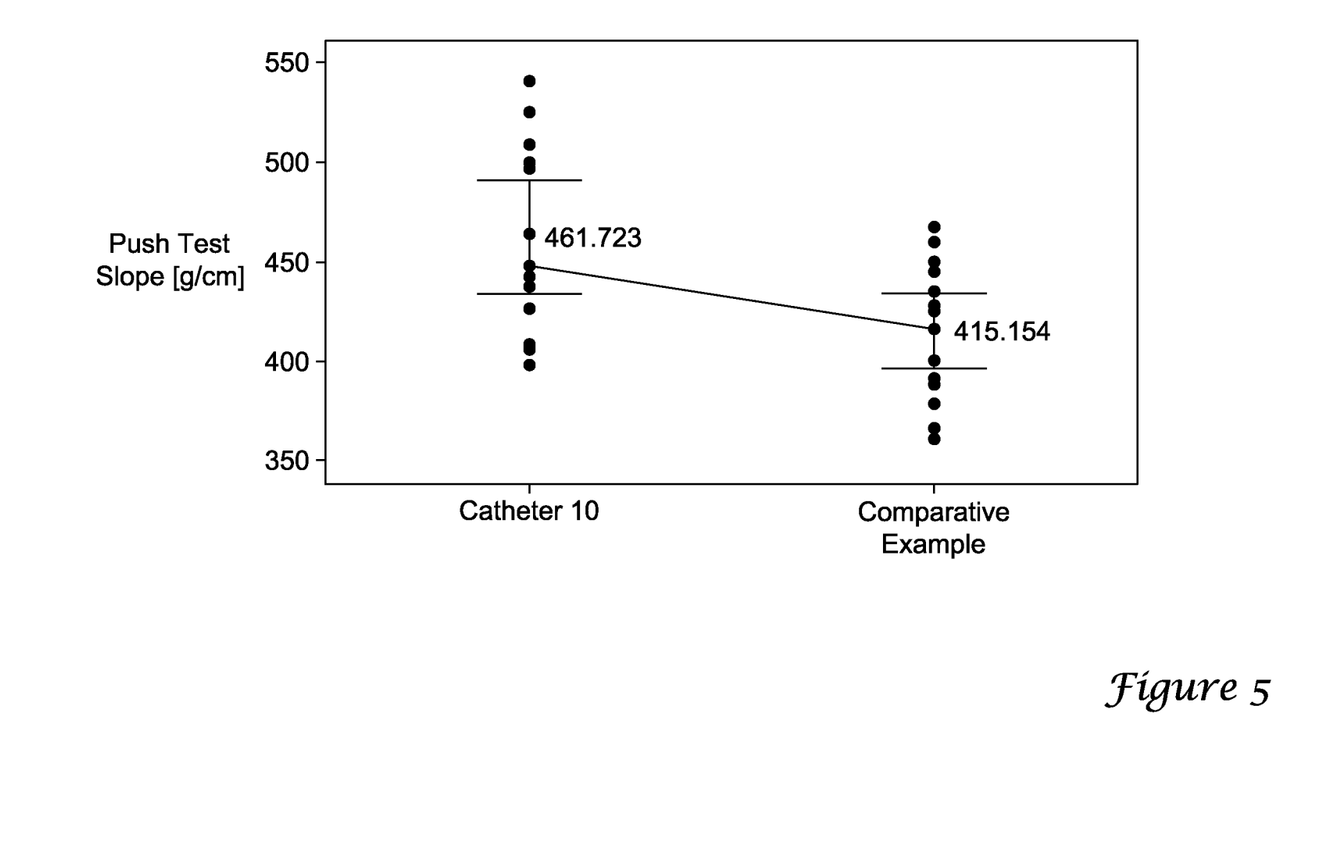
FIG. 5 is a graph depicting the results of a push test for the catheter illustrated in FIGS. 1-4 compared to another catheter.

Core wire 33 and catheter shaft 12 may be attached at a plurality of discrete bond points 35. The number of bond points 35 may vary. For example, core wire 33 and catheter shaft 12 may be attached at 2, 3, 4, 5, 6, 7, 8, 9, 10, or more discrete bond points 35. Each of the bond points may be spaced from one another. As alluded to above, the discrete bond points 35 may be discrete thermal bonds, laser bonds, welds, combinations thereof, or the like. Such bonding between core wire 33 and catheter shaft 12 (e.g., midshaft portion 16) was found to increase the pushability of catheter 10. Indeed, catheter 10 was tested for pushability using a standard catheter push test and was found to have about a 10% increase (e.g., about 11.1%) in pushability (e.g., greater force transmission per unit displacement) over comparable example catheters that did not include a core wire that was bonded to the midshaft portion. The results of the push test for catheter 10 (along with comparative example catheters lacking a core wire that was bonded to the midshaft) is depicted in FIG. 5.

To facilitate the bonding between core wire 33 and catheter shaft 12, a sleeve or jacket 37 may be disposed on core wire 33. Sleeve 37 may relatively thin wall thickness so as to have a relatively low impact on fluid flow through inflation lumen 30. In some embodiments, sleeve 37 and/or core wire 33 may be longitudinally stretched, which may increase the mechanical engagement of sleeve 37 and core wire 33 and thereby improve the force transmission along catheter shaft 12 (e.g., from proximal shaft portion 14 to distal shaft portion 18). Stretching sleeve 37 may also thin the wall thickness of sleeve 37, which may further reduce any potential impact on fluid flow through inflation lumen 30.

Sleeve 37, which may be a polymer sleeve, may bond to the inner surface of midshaft portion 16 and, thus, bond core wire 33 to midshaft portion 16. For example, a thermal bond (e.g., initiated via a laser) may allow sleeve 37 to melt and bond with midshaft portion 16 and secure core wire 33. In some embodiments, sleeve 37 may include a colorant, which may help improve bonding between core wire 33 and midshaft portion 16. In some of these and in other embodiments, sleeve 37 may include an infrared energy absorbing material. For example, sleeve 37 may include CLEARWELD®, which is commercially available from Gentex Corporation (Carbondale, Pa.) or similar materials. The infrared absorbing material may be extruded (e.g., co-extruded) with the sleeve 37 material or the infrared absorbing material may be applied to sleeve 37 (e.g., via spraying or other suitable application methods). The use of such materials may further improve the ability of core wire 33 to be bonded (e.g., welded) with midshaft portion 16. For example, application of infrared energy to catheter shaft 12 may allow core wire 33 to bond with midshaft portion 16.

Core wire 33 may generally take the form of a wire or rod. In some embodiments, core wire 33 may have a substantially uniform diameter. In other embodiments, core wire 33 may include one or more tapers or other changes in outer diameter. For example, the distal portion of core wire 33 may taper. In addition, core wire 33 may be a singular wire having a solid cross-section. In other embodiments, core wire 33 may be tubular or include portions that are tubular. In still other embodiments, core wire 33 may include a plurality of wire filaments that may be longitudinally aligned, twisted, braided, or the like.

The materials used for core wire 33 may include a metal. This may include any of the metals, to the extent appropriate, disclosed herein. For example, core wire 33 may include stainless steel, nickel-titanium alloy, or the like. In other embodiments, core wire 33 may include a relatively stiff polymer. This may include any of the polymers, to the extent appropriate, disclosed herein. For example, core wire 33 may include polyimide, polyetheretherketone, or any other suitable material.

Figure 6:
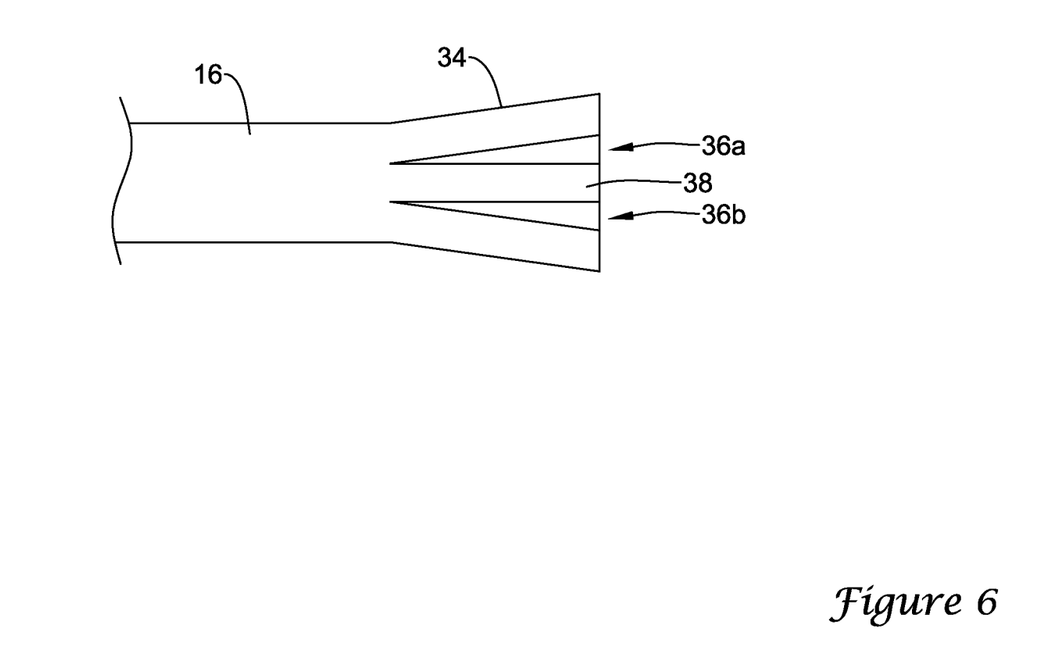
FIGS. 6-11 illustrate some of the example method steps for manufacturing the balloon catheter shown in FIG. 1-5.

FIGS. 6-11 illustrate some of the processing steps that may be utilized to form catheter 10 and/or catheter shaft 12. For example, FIG. 6 shows part of midshaft portion 16. Here it can be seen that a distal end 34 of midshaft portion 16 may be flared or otherwise enlarged. In addition, one or more cuts or slots, for example cuts 36a/36b, may be formed in distal end 34 of midshaft portion 16. A tongue 38 may be defined between cuts 36a/36b.

Figure 7:
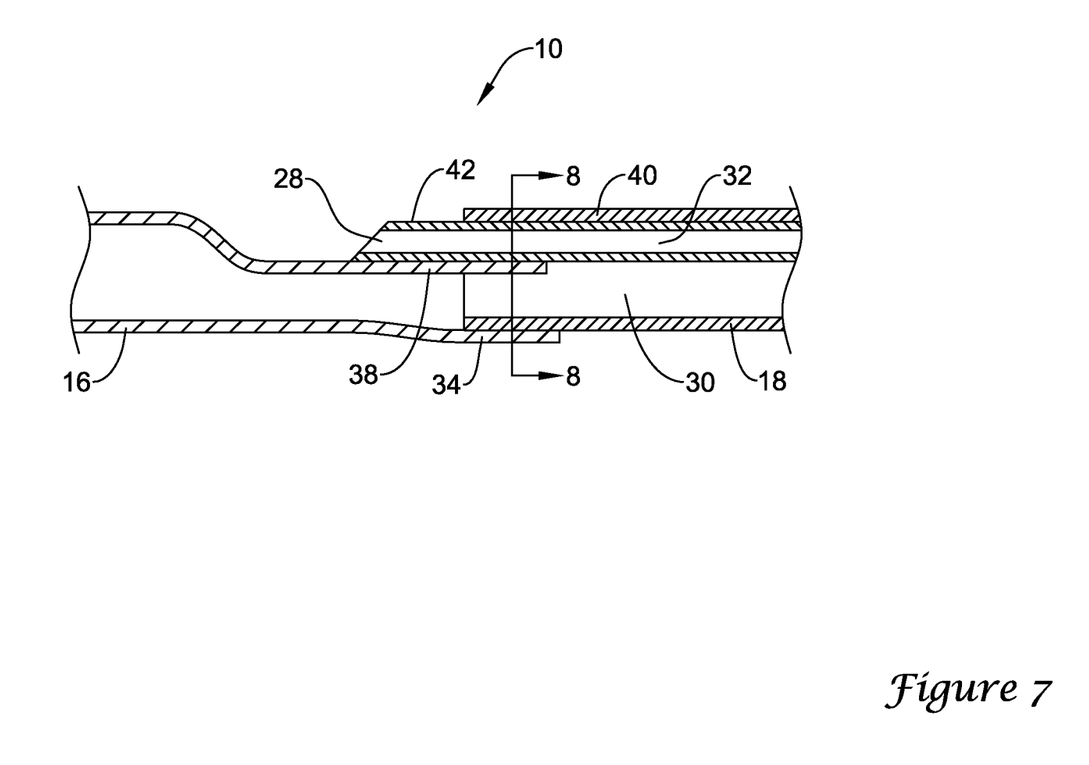
Figure 8:
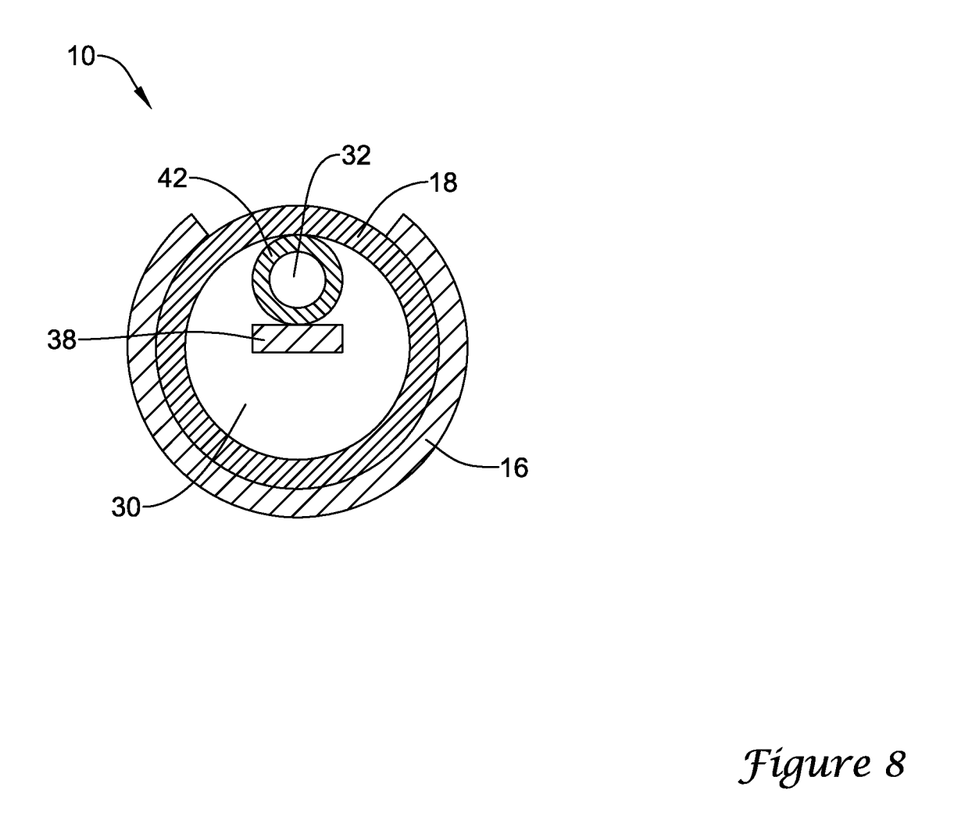

A proximal end 40 of distal shaft portion 18 may be disposed within the enlarged distal end 34 of midshaft portion 16 as shown in FIG. 7. In doing so, tongue 38 may be pressed inward and form a shelf or ledge. A distal inner tube 42 may be disposed within distal shaft portion 18 and may rest upon the ledge formed by tongue 38. Distal inner tube 42 may ultimately form guidewire lumen 32 as described in more detail below. The arrangement of distal inner tube 42 relative to tongue 38, midshaft portion 16, and distal shaft portion 18 can also be seen in FIG. 8.

Figure 9:
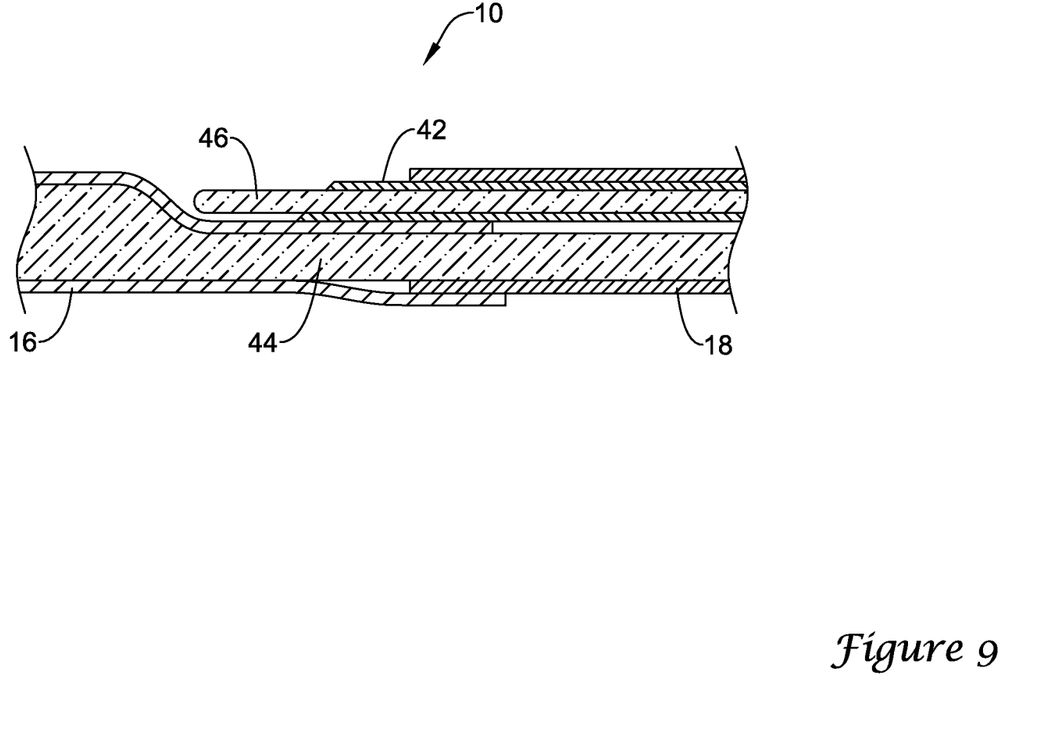
Figure 10:
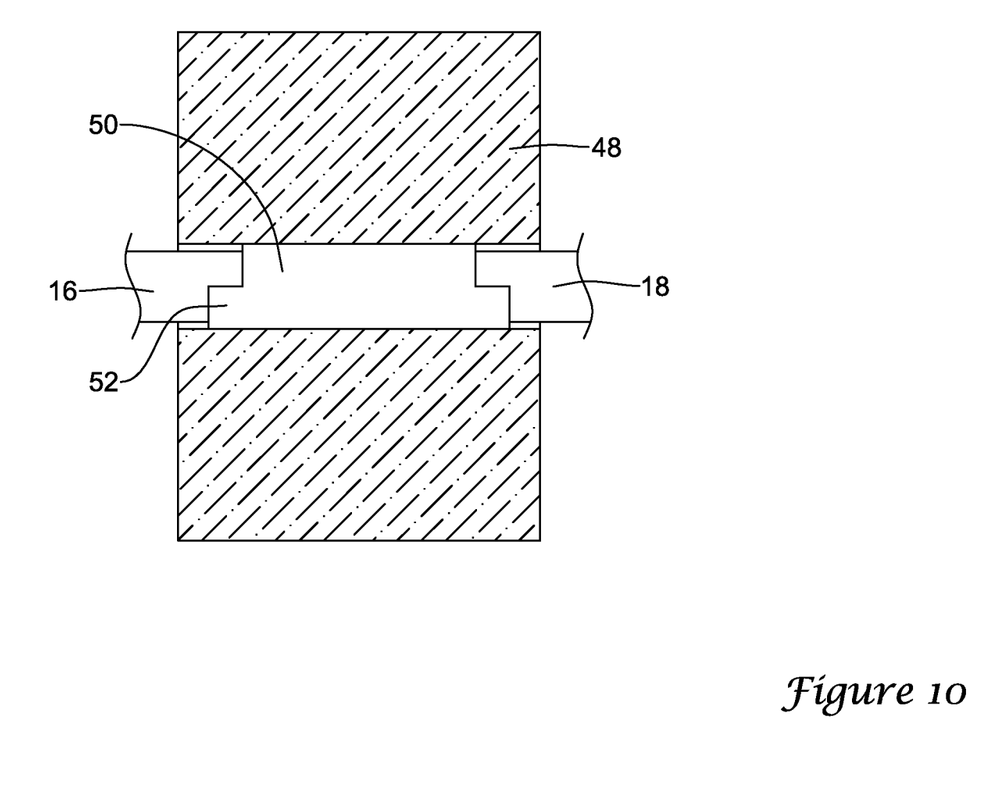
Figure 11:
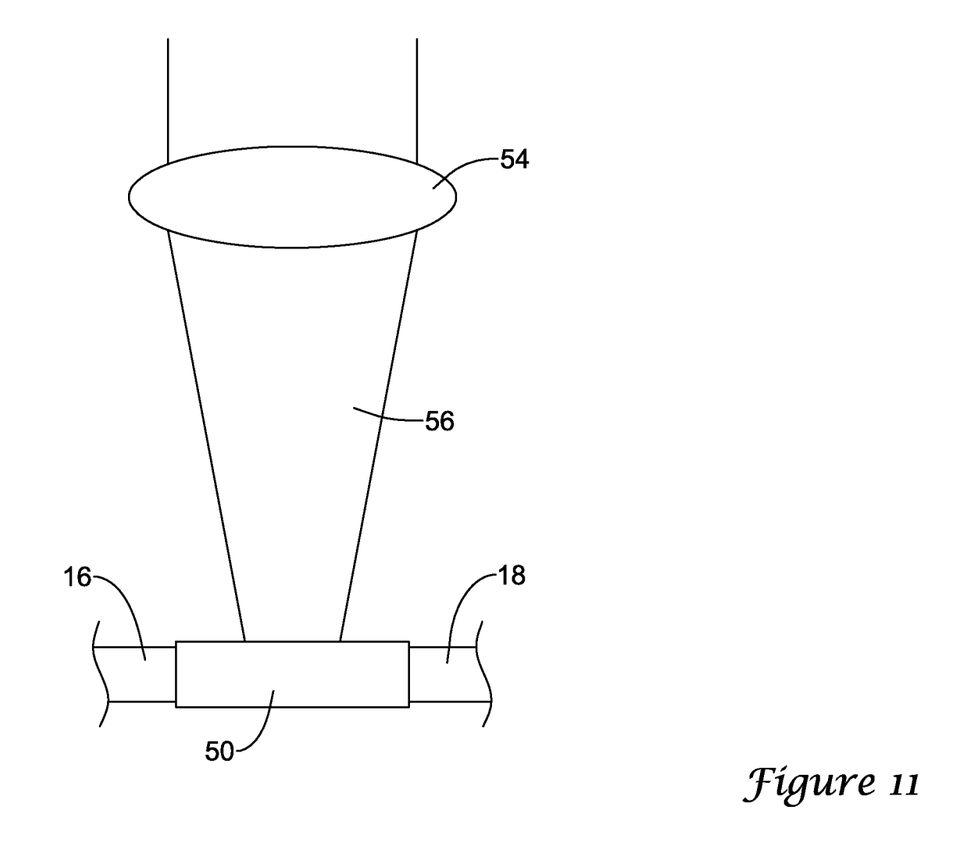

When suitably arranged, a first mandrel 44 may be inserted within a portion of distal shaft portion 18 and midshaft portion 16 as shown in FIG. 9. Likewise, a second mandrel 46 may be inserted within distal inner tube 42. With mandrels 44/46 in place, midshaft portion 16 and distal shaft portion 18 may be disposed within a compression fixture 48 as shown in FIG. 10. A sleeve 50 may be disposed over a region of midshaft portion 16 and distal shaft portion 18. Sleeve 50 may include one or more flanking ears 52, which may aid in removal of sleeve 50 upon completion of the manufacturing process. Finally, heat may be applied to sleeve 50. This may include the use of a lens 54 to focus heat (e.g., laser energy 56) onto sleeve 50 as depicted in FIG. 11. When heated, midshaft portion 16, distal shaft portion 18, and distal inner tube 42 may melt together. Mandrels 44/46 can be removed, thereby defining inflation lumen 30 and guidewire lumen 32, respectively, and the result may be the formation of catheter shaft 12 as shown in FIGS. 1-3.

The materials that can be used for the various components of catheter 10 may include those commonly associated with medical devices. For simplicity purposes, the following discussion makes reference to catheter shaft 12 and other components of catheter 10. However, this is not intended to limit the devices and methods described herein, as the discussion may be applied to other similar tubular members and/or components of tubular members or devices disclosed herein.

Catheter shaft 12 and/or other components of catheter 10 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of catheter shaft 12 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of catheter 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of catheter 10 to achieve the same result.

In some embodiments, a degree of Magnetic Resonance Imaging (MRI) compatibility is imparted into catheter 10. For example, catheter shaft 12, or portions thereof, may be made of a material that does not substantially distort the image and create substantial artifacts (i.e., gaps in the image). Certain ferromagnetic materials, for example, may not be suitable because they may create artifacts in an MRI image. Catheter shaft 12, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of catheter shaft 12 that may define a generally smooth outer surface for catheter 10. In other embodiments, however, such a sheath or covering may be absent from a portion of all of catheter 10, such that catheter shaft 12 may form the outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the catheter 10 (including, for example, the exterior surface of catheter shaft 12) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of catheter shaft 12, or other portions of catheter 10. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

The entire disclosures of U.S. Pat. Nos. 6,409,863, 5,156,594, 5,720,724, 6,361,529, and 6,475,187 are herein incorporated by reference.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A balloon catheter, comprising:
 a proximal shaft;
 a midshaft attached to the proximal shaft, wherein the midshaft has an outer wall;
 a distal shaft attached to the midshaft;
 a balloon coupled to the distal shaft;
 wherein an inflation lumen is defined that extends from the proximal shaft, through the midshaft, and into the distal shaft, the inflation lumen being in fluid communication with the balloon;
 a core wire disposed within the inflation lumen and attached to the midshaft, the core wire extending continuously from the proximal shaft, through the midshaft, and into the distal shaft; and a single polymer sleeve disposed on an outer surface of the core wire, the polymer sleeve attached to only one longitudinal region of the midshaft, leaving a majority of the inflation lumen open;

wherein the inflation lumen extends between an outer surface of the polymer sleeve and an inner surface of the midshaft.

2. The balloon catheter of claim 1, wherein the core wire is attached to the midshaft with an adhesive.

3. The balloon catheter of claim 1, wherein the core wire is attached to the midshaft with a thermal bond.

4. The balloon catheter of claim 1, wherein the core wire is attached to the midshaft with a laser bond.

5. The balloon catheter of claim 1, wherein the sleeve includes an infrared energy absorbing material.

6. The balloon catheter of claim 1, wherein the core wire is attached to the midshaft with a plurality of discrete bonds.

7. The balloon catheter of claim 1, further comprising a guidewire port disposed in the midshaft, wherein a distal end of the polymer sleeve is proximal of the guidewire port.

8. A balloon catheter, comprising:
a catheter shaft having a distal region and an inner wall surface defining an inflation lumen;
a balloon attached to the distal region, the balloon being in fluid communication with the inflation lumen;
a core wire disposed within the inflation lumen, the core wire being attached to the inner wall surface at a plurality of discrete bond points; and
a single polymer sleeve disposed on an outer surface of the core wire, the polymer sleeve attached to only one longitudinal region of the inner wall surface leaving a majority of the inflation lumen open, the polymer sleeve defining at least one of the plurality of discrete bond points between the core wire and the inner wall surface;
wherein the inflation lumen extends between the inner wall surface and an outer surface of the polymer sleeve.

9. The balloon catheter of claim 8, wherein the core wire is attached to the inner wall surface with a plurality of discrete adhesive bond points.

10. The balloon catheter of claim 8, wherein the core wire is attached to the inner wall surface with a plurality of discrete thermal bond points.

11. The balloon catheter of claim 8, wherein the core wire is attached to the inner wall surface with a plurality of discrete laser bond points.

12. The balloon catheter of claim 8, wherein the sleeve includes an infrared energy absorbing material.

13. The balloon catheter of claim 8, further comprising a guidewire port disposed in the distal region, wherein a distal end of the polymer sleeve is proximal of the guidewire port.

* * * * *